United States Patent [19]

Bergeron, Jr.

[11] Patent Number: 5,677,351

[45] Date of Patent: Oct. 14, 1997

[54] STERICALLY HINDERED TETRAAMINES AND METHOD FOR THEIR PRODUCTION

[75] Inventor: Raymond J. Bergeron, Jr., Gainesville, Fla.

[73] Assignee: University of Florida Research Foundation, Inc., Gainesville, Fla.

[21] Appl. No.: 479,505

[22] Filed: Jun. 7, 1995

Related U.S. Application Data

[60] Division of Ser. No. 231,692, Apr. 25, 1994, which is a continuation-in-part of Ser. No. 834,345, Feb. 12, 1992, Pat. No. 5,342,945, which is a division of Ser. No. 210,520, Jun. 23, 1988, Pat. No. 5,091,576, which is a continuation-in-part of Ser. No. 66,227, Jun. 25, 1997, abandoned, which is a continuation-in-part of Ser. No. 936,835, Dec. 2, 1986, abandoned.

[51] Int. Cl.$^6$ .................. A61K 31/13; A61K 31/135; C07C 211/13; C07C 211/27
[52] U.S. Cl. .................. 514/674; 514/655; 514/654; 514/646; 564/512; 564/367
[58] Field of Search .................. 514/654.5, 674, 514/646; 564/512, 305, 367, 336, 368, 374

[56] References Cited

U.S. PATENT DOCUMENTS

| | | | |
|---|---|---|---|
| 2,267,204 | 12/1941 | Kgrides | 514/674 |
| 2,279,294 | 4/1942 | Hardman | 564/337 |
| 4,321,190 | 3/1982 | Constanzi et al. | 524/252 |
| 4,507,321 | 3/1985 | Raisfeld | 514/673 |
| 4,591,605 | 5/1986 | Ray | 514/579 |
| 5,109,024 | 4/1992 | Prakash et al. | 514/674 |
| 5,217,964 | 6/1993 | Edwards et al. | 514/104 |
| 5,434,145 | 7/1995 | Edwards et al. | 514/108 |

OTHER PUBLICATIONS

Weinstork et al, "Synthesis of New Polyamines Derivatives for Cancer Chemotherapeutic Studies", Journal of Pharm. Sciences, vol. 70, No. 8 (1981).

*Primary Examiner*—Kimberly J. Prior
*Assistant Examiner*—Deborah Lambkin
*Attorney, Agent, or Firm*—Kerkam, Stowell, Kondracki & Clarke; Dennis P. Clarke

[57] ABSTRACT

Polyamines having the formula:

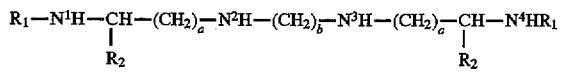

wherein $R_1$ and $R_2$ are alkyl, aralkyl or aryl having up to 10 carbon atoms; and a and b may be the same or different and are integers from 1 to 8; or a salt thereof with a pharmaceutically acceptable acid. Anti-neoplastic, anti-diarrheal, anti-peristaltic, gastrointestinal anti-spasmodic, anti-viral, anti-retroviral, anti-psoriasis and insecticidal compositions comprising biologically effective amounts of the above-described amines and biologically acceptable carriers therefor are also disclosed, as well as methods of treatment, administration or application of biologically effective amounts of the polyamines of the invention. Also disclosed are methods for preparing the polyamines of the invention.

8 Claims, 1 Drawing Sheet

STERICALLY HINDERED TETRAAMINES AND METHOD FOR THEIR PRODUCTION

BACKGROUND OF THE INVENTION

Related Applications

This is a division of application Ser. No. 08/231,692 filed Apr. 25, 1994, which is a continuation-in-part of application Ser. No. 07/834,345 filed Feb. 12, 1992 (now U.S. Pat. No. 5,342,945 issued Aug. 30, 1994), which is a division of application Ser. No. 07/210,520 filed Jun. 23, 1988 (now U.S. Pat. No. 5,091,576 issued Feb. 25, 1992), which is a continuation-in-part of application Ser. No. 07/066,227 filed Jun. 25, 1987 (now abandoned), which is a continuation-in-part of application Ser. No. 06/936,835 filed Dec. 2, 1986 (now abandoned).

FIELD OF THE INVENTION

The present invention relates to novel polyamines having anti-neoplastic, anti-diarrheal, anti-peristaltic, gastrointestinal anti-spasmodic, anti-viral, anti-retroviral, anti-psoriasis and insecticidal activities, as well as pharmaceutical compositions and methods of treatment based thereon and methods for their preparation.

In recent years, a great deal of attention has been focussed on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta., Vol. 473, p. 241 (1978); Fillingame et al, Proc. Natl. Acad. Sci. U.S.A., Vol. 72, p. 4042 (1975); Metcalf et al, J. Am. Chem. Soc., Vol. 100, p. 2551 (1978); Flink et al, Nature (London), Vol. 253, p. 62 (1975); and Pegg et al, Polyamine Metabolism and Function, Am. J. Cell. Physiol., Vol. 243, pp. 212–221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, Science, Vol. 149, p. 48 (1965); Russell et al, Polyamines as Biochemical Markers of Normal and Malignant Growth (Raven, New York, 1978); Hirschfield et al, J. Bacteriol., Vol. 101, p. 725 (1970); Hafner et al, J. Biol. Chem., Vol. 254, p. 12419 (1979); Cohn et al, J. Bacteriol., Vol. 134, p. 208 (1978); Pohjatipelto et al, Nature (London), Vol. 293, p. 475 (1981); Mamont et al, Biochem. Biophys. Res. Commun., Vol. 81, p. 58 (1978); Bloomfield et al, Polyamines in Biology and Medicine (D. R. Morris and L. J. Morton, eds., Dekker, New York, 1981), pp. 183–205; Gosule et al, Nature, Vol. 259, p. 333 (1976); Gabbay et al, Ann. N.Y. Acad. Sci., Vol. 171, p. 810 (1970); Suwalsky et al, J. Mol. Biol., Vol. 42, p. 363 (1969); and Liquori et al, J. Mol. Biol., Vol. 24, p. 113 (1968).

However, regardless of the reason for increased polyamine levels, the phenomenon can be and has been exploited in chemotherapy. See Sjoerdsma et al, Butterworths Int. Med. Rev.: Clin. Pharmacol. Thera., Vol. 35, p. 287 (1984); Israel et al, J. Med. Chem., Vol. 16, p. 1 (1973); Morris et al, Polyamines in Biology and Medicine; Dekker, New York, p. 223 (1981); and Wang et al, Biochem. Biophys. Res. Commun., Vol. 94, p. 85 (1980).

It is an object of the present invention to provide novel polyamines having a wide variety of biological activities.

It is another object of the present invention to provide novel compositions and methods of treatment and application based on the biological activities of the polyamines of the invention.

It is an additional object of the invention to provide novel methods for preparing the polyamines of the invention.

SUMMARY OF THE INVENTION

Figure 1:
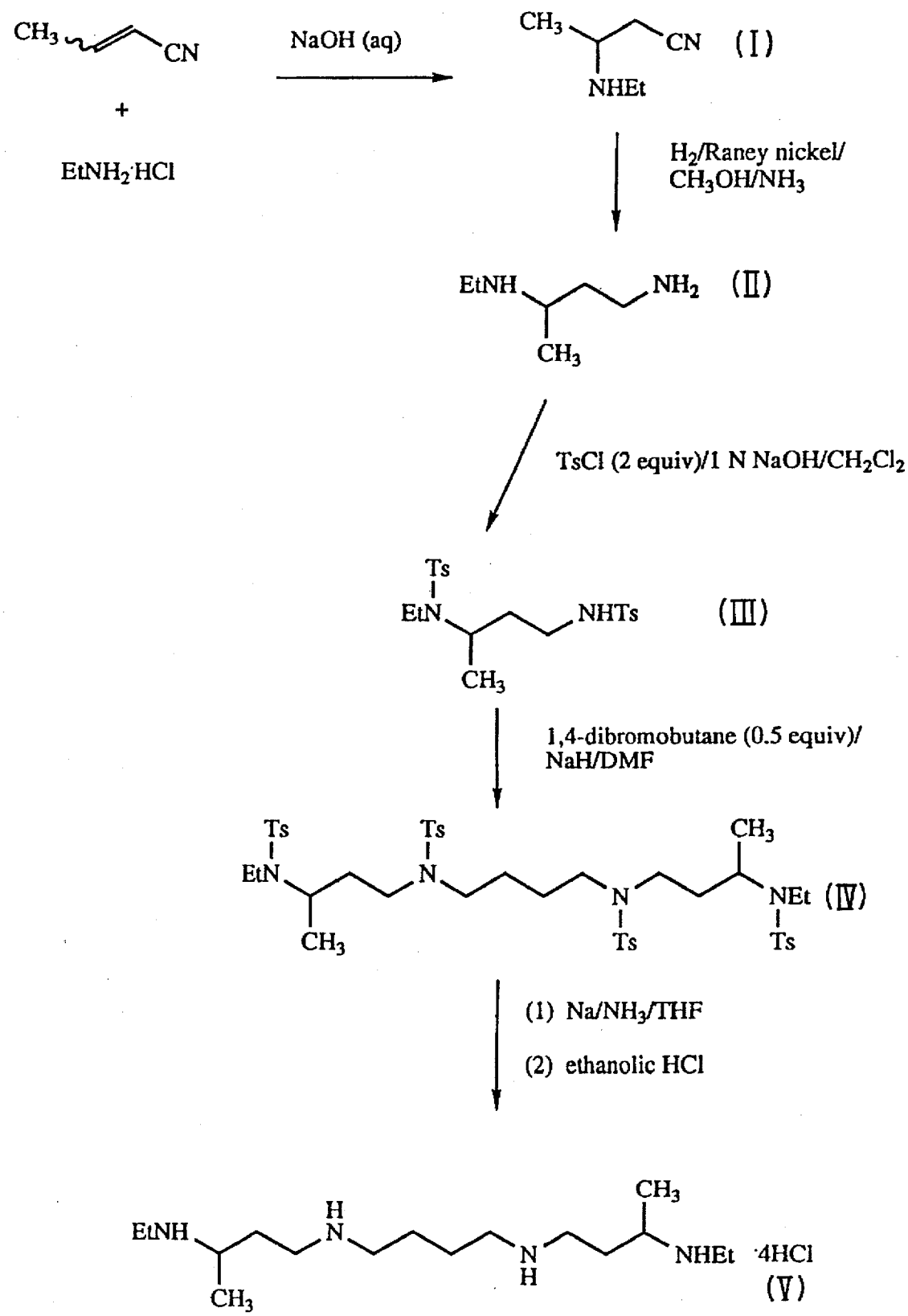
FIG. 1 is a diagram of a reaction scheme for preparing the polyamines of the invention.

The above and other objects are realized by the present invention, one embodiment of which comprises a polyamine having the formula:

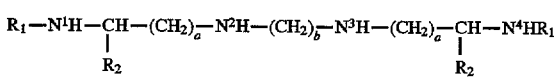

wherein $R_1$ and $R_2$ are alkyl, aralkyl or aryl having up to 10 carbon atoms; and a and b may be the same or different and are integers from 1 to 8; or a salt thereof with a pharmaceutically acceptable acid.

Further embodiments of the invention relate to anti-neoplastic, anti-diarrheal, anti-peristaltic, gastrointestinal anti-spasmodic, anti-viral, anti-retroviral, anti-psoriasis and insecticidal compositions comprising biologically effective amounts of the above-described amines and biologically acceptable carriers therefor.

Still further embodiments of the invention comprise methods of treatment, administration or application of biologically effective amounts of the polyamines of the invention.

Final embodiments of the invention relate to methods for preparing the polyamines described above comprising:

1. reacting a compound having the formula:

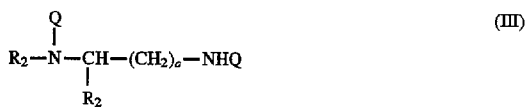

(III)

with a compound having the formula:

wherein Q is an amine protective group, e.g., tosyl, mesitylene sulfonyl, and the like, X is a leaving group, e.g., Cl, Br, I, O-tosyl, and the like, which can be displaced with the $-N^{\ominus}-Q$ anion of compound (III), and $R_1$, $R_2$ and a have the meanings ascribed above to produce a compound of the formula:

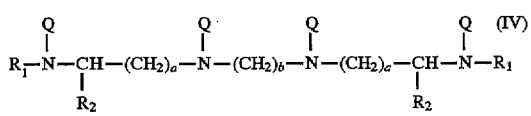

and 2. deprotecting compound (IV) to remove said Q groups to produce the polyamines of the invention.

The above method may optionally include the preliminary steps of:

3. reducing a compound of the formula:

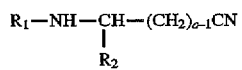

to produce a compound of the formula:

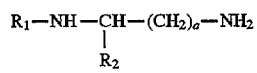

and 4. reacting the amino groups of compound (II) with a reagent to produce a compound having the formula of compound (III).

DETAILED DESCRIPTION OF THE INVENTION

The polyamines of the present invention possess virtually the same biological activities as the corresponding polyamines described in U.S. patent application Ser. Nos. 07/834,345 filed Feb. 12, 1992; 07/066,227 filed Jun. 25, 1987; and 06/936,835 filed Dec. 2, 1986.

Polyamines corresponding to those of the invention wherein $R_1$ and $R_2$ are hydrogen are metabolized by the body when administered to human and non-human patients. The metabolic products of these polyamines are more toxic than the parent compounds.

The steric hindrance provided by the $R_2$ groups renders the polyamines of the present invention difficult to metabolize, thereby extending the half-life of the polyamine drug in the body and reducing the potential toxic side effects accompanying the metabolic products thereof.

Referring to FIG. 1, the polyamines of the present invention are prepared by the novel method described below.

Compound (I) is prepared by the conjugate addition of an alkyl amine with an appropriate unsaturated nitrile to produce an intermediate nitrile amine according to the reaction scheme:

$$CH_3-CH=CH-CN + CH_3CH_2NH_2 \longrightarrow (I)$$

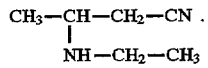

An alternate synthesis of compound (I) is found in Kurihara et al, J. Pharm. Soc. Japan, Vol. 75, pages 1267-1269 (1955); and Chem. Abs., Vol. 50:8636b (1956).

The cyano group of the intermediate is then reduced (e.g., $H_2$, Raney nickel in methanolic $NH_3$) to produce the intermediate:

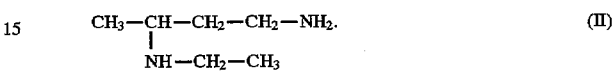

The latter is reacted with a suitable reagent which provides an amine protective group on the nitrogen atoms thereof [e.g., tosyl (Ts) chloride, mesitylene sulfonyl chloride, and the like], thereby producing a compound of the formula:

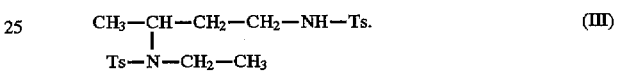

A compound having termini which can N-alkylate the anion of compound (III),

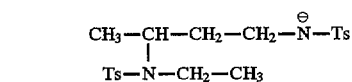

e.g., dibromobutane, is then reacted with compound (III) (in NaH, DMF) to produce a tetratosyl polyamine having the formula:

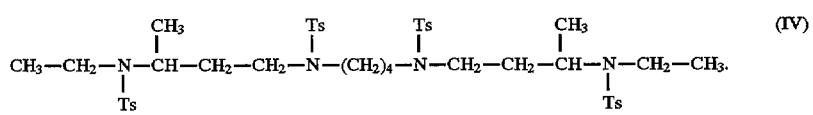

The protective tosyl (Ts) groups are removed (e.g., Na, $NH_3$, THF) to yield the polyamine:

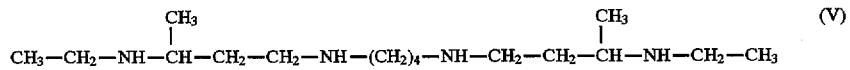

The polyamines are preferably utilized as their acid addition salts with pharmaceutically acceptable acids, e.g., HCl, p-toluene sulfonic acid, methylene sulfonic acid, and the like.

In the structural formulae set forth herein, the terms "aryl" and "aralkyl" are intended to embrace any aromatic group whose chemical and physical properties do not adversely affect the biological activities of the polyamines and which do not adversely affect the efficacy and safety of the polyamines for therapeutic applications.

The anti-neoplastic activity (L1210) of the polyamines of the present invention was compared with that of the corresponding $N^1$, $N^4$-unsubstituted polyamines according to the following method and was found to be of about equal quality.

Murine L1210 leukemia cells were maintained in logarithmic growth as a suspension culture in RPMI 1640 containing 2% HEPES-MOPS buffer and 10% fetal calf serum as described by Porter et al, Science, Vol. 219, pages 1083–1085 (1983). Cultures were treated while in logarithmic growth (0.5 to $1\times10^5$ cells/mL) with the test compounds at concentrations ranging from $10^{-6}$ to $10^{-2}$M. After 48 and 96 hours, cells were counted by electronic particle analysis and viability determinations with trypan blue.

The results are set forth in Table 1 below.

TABLE 1

| | L1210 | | |
|---|---|---|---|
| Polyamine Analogue IC$_{50}$ (μM) | 48 h | 96 h | K$_i$ (μM) |
| 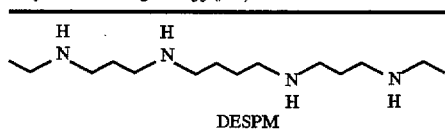 DESPM | 30 | 0.18 | 1.6 |
| 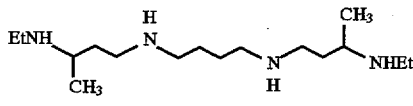 "crotyl" DESOM, or 1,12-diMe DESPM (4) | 50 | 0.1 | — |

The invention is illustrated by the following non-limiting examples, wherein silica gel 60 (70–230 mesh) was used for column chromatography. Proton NMR spectra were recorded on a Varian EM-390 instrument and were run in CHCl$_3$ or D$_2$O with chemical shifts given in parts per million downfield from an internal tetramethylsilane or HOD (δ 4.7) standard, respectively (coupling constants are in hertz).

EXAMPLE 1

3-(N-Ethylamino)butanenitrile (I). 50% NaOH (w/w, 32 mL) was cautiously added to ethylamine hydrochloride (44.13 g, 0.54 mol) at 0° C. Crotononitrile (cis and trans, 25 mL, 0.31 mol) was added to the cold suspension over 3 min., and the mixture was stirred for 18 hours (0° C. to room temperature). The reaction was heated on a boiling water bath for 1 hour 20 min. and allowed to cool. Ether (100 mL) was added, and then 1 N NaOH (50 mL) was added. The layers were separated, and the aqueous phase was further extracted with ether (2×100 mL). The combined organic portion was washed with brine (50 mL). The brine was extracted with ether (4×50 mL) and all of the organic extracts were evaporated in vacuo. A short path distillation of the crude product afforded 19.25 g (55%) of I bp 38°–45.5° C./0.06 mm. NMR δ 1.00–1.32 (m, 7 H), 2.42 (d, 2 H, J=6), 2.63 (q, 2 H, J=7), 3.03 (sextet, 1 H, J=6).

N-Ethyl-1-methyl-1,3-diaminopropane dihydrochloride (II). Raney nickel (W-2 grade, 13.18 g) and then concentrated NH$_4$OH (50 mL) were added to a solution of I (19.21 g, 0.171 mol) in methanol (207 mL) in a 500 mL Parr bottle. The suspension was cooled to 0° C., and ammonia was gently bubbled in for 40 min. Hydrogenation was carried out on a Parr shaker for 10 hours at 50–55 psi. The catalyst was filtered off (Celite) and the filtrate was concentrated. Bulb to bulb distillation of the crude product, up to 66° C./0.005 mm, followed by addition of EtOH and concentrated HCl (35 mL), and evaporation and drying gave 29.11 g (90%) of II as a white solid. NMR (D$_2$O) δ 1.28–1.55 (m, 6 H), 1.8–2.5 (m, 2 H), 3.12–3.75 (m, 5 H).

N,N'-Bis(p-toluenesulfonyl)-N-ethyl-1-methyl-1,3-diaminopropane (III). A solution of p-toluenesulfonyl chloride (17.01 g, 89.2 mmol) in CH$_2$Cl$_2$ (300 mL) was added to a solution of II (8.89 g, 47.0 mmol) in 1N NaOH (300 mL) which had been cooled to 0° C. After addition was complete, the biphasic mixture was stirred for 14 hours (0° C. to room temperature). The layers were separated and the aqueous portion was extracted with CH$_2$Cl$_2$ (2×50 mL). The combined organic phase was washed with 1N HCl (2×100 mL) and (100 mL) and evaporated in vacuo. Column chromatography on silica gel eluting with 3% EtOH/CHCl$_3$ produced 7.46 g (39%) of III. NMR δ 0.77 (d, 3 H, J=7), 1.15 (t, 3 H, J=7), 1.45–1.76 (m, 2 H), 2.40 (s, 6 H), 2.79–3.25 (m, 4 H), 3.70–4.08 (m, 1 H), 5.47 (t, 1 H, J=7), 7.13–7.81 (m, 8 H).

Anal. calcd. for C$_{20}$H$_{28}$N$_2$O$_4$S$_2$: C, 56.58; H, 6.65; N, 6.60. Found: C, 56.60; H, 6.64; N, 6.65.

N$^1$,N$^{12}$-Diethyl-1,12-dimethyl-N$^1$,N$^4$,N$^9$,N$^{12}$-tetra (p-toluenesulfonyl)spermine (IV). Sodium hydride (80% in oil, 0.45 g, 15.0 mmol) was added to a solution of III (4.98 g, 11.7 mmol) in DMF (95 mL). The suspension was stirred for 6 min. at room temperature. 1,4-Dibromobutane (0.65 mL, 5.44 mmol) was introduced and the reaction mixture was heated at 80° C. for 4.5 hours. After cooling to 0° C., excess EtOH was cautiously added to quench residual NaH, and solvents were removed under high vacuum. 1N NaOH (100 mL) was added to the residue, followed by extraction with CH$_2$Cl$_2$ (3×100 mL). The combined organic phase was washed with H$_2$O (100 mL) and evaporated in vacuo. Column chromatography on silica gel eluting with 1.5% CH$_3$OH/CHCl$_3$ led to 2.55 g (52%) of IV as a white amorphous solid. NMR δ 0.91 (d, 6 H, J=7), 1.24 (t, 6 H, J=7), 1.45–1.95 (m, 8 H), 2.37 and 2.39 (2 s, 12 H), 2.9–3.3 (m, 12 H), 3.63–4.05 (m, 2 H), 7.1–7.8 (m, 8 H).

N$^1$,N$^{12}$-diethyl-1,12-dimethylspermine (V). A solution of IV (2.54 g, 2.81 mmol) in dry THF (150 mL) was cooled to −78° C. under N$_2$. Ammonia (450 mL) was condensed using a dry ice condenser and then sodium (2.93 g, 0.127 mol) was added in portions. After the reaction was stirred for 1 day (−78° C. to room temperature), EtOH (100 mL) was added at 0° C., and solvents were removed, followed by extraction with CH$_2$Cl$_2$ (3×200 mL). The organic portion was evaporated and the residue was distilled (bulb to bulb, up to 123° C./0.005 mm), followed by the addition of EtOH and concentrated HCl (2 mL) and evaporation, giving crude tetrahydrochloride salt (V). The product was converted to its tetra(tert-butoxycarbonyl) derivative (BOC-ON, NEt₃, aq THF), Which was purified by column chromatography on silica gel eluting with 4% EtOH/CHCl₃. BOC group removal (TFA), extraction as above and treatment with ethanolic HCl furnished 0.38 g (31%) of V as a white solid. NMR (D₂O) δ 1.2–1.5 (m, 12 H), 1.68–2.37 (m, 8 H), 2.98–3.67 (m, 14 H).

Anal. calcd. for $C_{16}H_{42}Cl_4N_4$; C, 44.45; H, 9.79; N, 12.96. Found: C, 44.37, H, 9.73, N, 12.94.

I claim:

1. A method of treating a human or non-human patient in need thereof comprising administering thereto an antidiarrheal, anti-peristaltic or gastrointestinal anti-spasmodic effective amount of a polyamine having the formula:

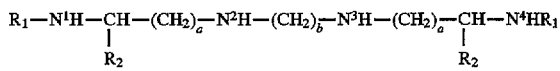

wherein: $R_1$ and $R_2$ are alkyl, hydrocarbyl aralkyl or hydrocarbyl aryl each having up to 10 carbon atoms; and a and b may be the same or different and are integers from 1 to 8; or a salt thereof with a pharmaceutically acceptable acid.

2. A method according to claim 1 wherein $R_2$ is methyl.

3. A method according to claim 1 wherein $R_2$ is ethyl, propyl or butyl.

4. A method according to claim 1 wherein $R_1$ is ethyl.

5. A method according to claim 1 wherein $R_1$ is methyl, propel or butyl.

6. A method according to claim 1 wherein a is 2 and b is 4.

7. A method according to claim 1 wherein a is 3 and b is 3.

8. A method according to claim 1 wherein a is 3 and b is 4.

* * * * *

UNITED STATES PATENT AND TRADEMARK OFFICE
CERTIFICATE OF CORRECTION

PATENT NO. : 5,677,351
DATED : October 14, 1997
INVENTOR(S) : Raymond J. BERGERON, JR.

It is certified that error appears in the above-identified patent and that said Letters Patent is hereby corrected as shown below:

On the title page, in the left-hand column under "[56] References Cited - U.S. PATENT DOCUMENTS," the first- and third-listed patentees should read -- Kyrides -- and -- Costanzi et al --, respectively.

On the title page, in the right-hand column under "OTHER PUBLICATIONS," the author's name should read -- Weinstock -- and in the title of the publication, "Polyamines" should read -- Polyamine --

In column 5, at the bottom of Table 1, "DESOM" should read -- DESPM --

In column 7, line 3: delete "Which" and insert -- which --

In column 8, line 12 [claim 5, line 2]: delete "propel" and insert -- propyl --

Signed and Sealed this

Fourteenth Day of April, 1998

Attest:

BRUCE LEHMAN

Attesting Officer

Commissioner of Patents and Trademarks